United States Patent [19]

Spielvogel et al.

[11] Patent Number: 5,272,250

[45] Date of Patent: Dec. 21, 1993

[54] BORONATED PHOSPHORAMIDATE COMPOUNDS

[76] Inventors: Bernard F. Spielvogel, 107 Wood Glen Dr., Cary, N.C. 27511; Anup Sood, 5041 Gatewood Dr., Durham, N.C. 27712

[21] Appl. No.: 911,218

[22] Filed: Jul. 10, 1992

[51] Int. Cl.$^5$ .................. C07K 5/04; C07K 7/04; C07F 9/02; A61K 37/02
[52] U.S. Cl. .................. 530/300; 530/324; 530/325; 530/326; 530/327; 530/328; 530/329; 530/330; 530/331; 530/350; 536/22.1; 536/25.5; 536/26.4; 536/24.5; 536/26.44; 536/26.7; 536/26.8; 558/72
[58] Field of Search .......... 558/72; 530/300, 324-331, 530/350; 536/22-29

[56] References Cited

U.S. PATENT DOCUMENTS

| | | | |
|---|---|---|---|
| 3,104,253 | 9/1963 | Reetz | 558/72 |
| 3,232,723 | 2/1966 | Dever et al. | 558/72 X |
| 3,450,798 | 6/1969 | Green et al. | 558/72 |
| 4,734,517 | 3/1988 | Phillion | 558/72 |

FOREIGN PATENT DOCUMENTS

| | | | |
|---|---|---|---|
| 91-00286 | 1/1991 | World Int. Prop. O. | 558/72 |

OTHER PUBLICATIONS

Ctahko et al, Izvest. Akad. Nauk S.S.R., (1962) pp. 919–920.

"Conjugates of Oligonucleotides and Modified Oligonucleotides: A Review of Their Synthesis and Properties"; *Bioconjugate Chemistry*; John Goodchild; May/-Jun. 1990, vol. 1, No. 3, pp. 165–187.

"Deoxynucleoside H-Phosphonate Diester Intermediates in the Synthesis of Internucleotide Phosphate Analogues"; *Tetrahedron Letters*; Brian C. Froehler; vol. 27, No. 46, pp. 5575–5578, 1986.

"Oligonucleotide N-Alkylphosphoramidates: Synthesis and Binding to Polynucleotides"; *Biochemistry*; Alfred Jäger, et al.; 1988, 27, pp. 7237–7246.

"Oligodeoxynucleoside Phosphoramidates and Phosphorothioates as Inhibitors of Human Immunodeficiency Virus"; *Proc. Natl. Acad. Sci, USA*; Sudhir Agrawal, et al.; vol. 85, pp. 7079–7083, Oct. 1988.

"Cationic Oligonucleotides"; *J. Am. Chem. Soc.*, 1988, 110, pp. 4470–4471; Robert L. Letsinger, et al.

"Cholesteryl-Conjugaed Oligonucleotides: Synthesis, Properties and Activity as Inhibitors of Replication of Human Immunodeficiency Virus in Cell Culture"; *Proc. Natl. Acad. Sci. USA*; Robert L. Letsinger, et al.; vol. 86, pp. 6553–6556, Sep., 1989.

"Phosphoramidate Analogues of DNA; Synthesis and Thermal Stability of Heteroduplexes"; B. Frochler, et al.; *Nucleic Acids Research*; vol. 16, No. 11, pp. 4831–4839 (1988).

*Primary Examiner*—Floyd D. Higel
*Attorney, Agent, or Firm*—Bell, Seltzer, Park & Gibson

[57] ABSTRACT

A class of pharmaceutically active boronated compounds are provided. The boronated compounds include boronated phosphoramidates, and boronated nucleosides, and oligomers thereof. The compounds are boronated by an aminoalkyl substituted polyborane, carborane, metallopolyborane or metallocarborane.

18 Claims, No Drawings

BORONATED PHOSPHORAMIDATE COMPOUNDS

FIELD OF THE INVENTION

This invention pertains to novel boron containing compounds having pharmaceutical activity. More specifically, compounds of the present invention include boronated phosphoramidates, and nucleosides and oligonucleotides thereof having antisense properties.

BACKGROUND OF THE INVENTION

Antimetabolites are a well known class of antineoplastic agents that function by interfering with nucleic acid synthesis and consequently, replication within the target cells. Some of these compounds structurally mimic biosynthetic precursors of the naturally occurring nucleic acids, which are essential for replication and cell survival. By replacing these precursors, but without exhibiting the same biological effect, these compounds disrupt replication resulting in the demise of the target cell.

Many antimetabolites have significant antiviral and antitumor activity and are incorporated in a variety of therapeutic regimens. But despite the therapeutic benefits of such compounds, their use is often accompanied by deleterious side effects, e.g. nausea, alopecia, and bone marrow depression. Accordingly, a great deal of interest has focused on synthesizing new analogues with improved therapeutic indexes.

We have recently discovered that boron containing nucleotides may be one class of improved nucleic acid analogues. Some exemplary boronated nucleotides are described in copending, commonly owned U.S. patent application Ser. No. 07/443,781 of B. Spielvogel, A. Sood, I. Hall, and B. Ramsay-Shaw titled "Oligoribonucleoside and Oligodeoxyribonucleoside Boranophosphates" and filed Nov. 30, 1989, which is incorporated herein by reference. There we describe, for example, boronated oligonucleotides that contain a boron functionality attached to internucleotide phosphorus.

Boron containing compounds are also useful in an antineoplastic regimen known as Boron Neutron Capture Therapy (BNCT). Soloway, A. H., Progress in Boron Chemistry; Steinberg, H., McCloskey, A. L. Eds.; the Macmillan Company: New York, 1964; Vol. 1, Chapter 203-234. BNCT requires two components (Boron-10 and low energy thermal neutrons) for a radiotoxic reaction. The inherent advantage is that each component can be manipulated independently to produce the desired radiation effect. Boron-10 has a high cross section for thermal neutrons and after neutron capture, the particles generated, Li and $\alpha$, are relatively large by radiation standards and thus have a relatively short track in tissue, 10-14 microns. The Boron-10 is nonradioactive and for use in BNCT, its compounds do not have to be cytotoxic towards tumor cells. Thermal neutrons have such low energy that they cannot ionize boron components per se. Upon neutron capture, however, the energy generated is sufficient to destroy the cell. The problem in making this procedure clinically effective has stemmed not from the concept, per se, but from lack of knowledge in medicinal chemistry, nuclear engineering and physics, immunology, physiology and pharmacology. The present invention arose from our continued research on new boron-containing compounds having pharmaceutical activity.

SUMMARY OF THE INVENTION

The present invention provides novel boronated compounds, i.e., boronated phosphoramidates, and nucleosides and oligonucleotides comprising a boronated phosphoramidate as a component, methods for their synthesis, methods for treating patients, and pharmaceutical formulations comprising such agents. The boronated compounds exhibit antisense properties.

The compounds in accordance with the invention are boronated with a boron-containing substituent selected from the group consisting of hydrolytically stable polyborane, carborane, metallopolyborane and metallocarborane compounds.

A first embodiment of the invention is a boronated compound according to the formula

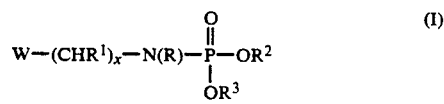

wherein:

R and $R^1$ are each independently selected from the group consisting of hydrogen, alkyl, and alkylaryl;

$R^2$ and $R^3$ are each independently selected from the group consisting of hydrogen, alkyl, alkylaryl, aryl, nucleosides and oligonucleotides; and W is polyborane or carborane, and wherein x is an integer from 1 to 20.

Boronated compounds of the present invention have pharmaceutical activity, including use in BNCT. Oligonucleotides of the present invention are useful as antisense agents.

A method for synthesizing boronated compounds of the invention is also disclosed. The method comprises reacting a phosphoramidate with an aminoalkyl substituted polyborane, carborane, metallopolyborane or metallocarborane of the formula W—(CHR$^1$)$_x$—N(-R)—, wherein W is polyborane, carborane, metallopolyborane or metallocarborane; $R^1$ and R are each independently hydrogen or $C_1$ to $C_{10}$ linear or branched alkyl or arylalkyl; and X is an integer from 1 to 20.

Another aspect of the present invention is a pharmaceutical formulation comprising boronated compounds of the invention or pharmaceutically acceptable salts thereof in a pharmaceutically acceptable carrier.

DETAILED DESCRIPTION OF THE INVENTION

The present invention provides novel pharmaceutical agents, i.e., boronated phosphoramidates, and nucleosides and oligonucleotides comprising a boronated phosphoramidate as a component, methods for their synthesis, methods for treating patients, and pharmaceutical formulations comprising such agents. The boronated compounds exhibit antineoplastic and antisense properties.

The compounds in accordance with the invention are boronated with a boron-containing substituent selected from the group consisting of hydrolytically stable polyborane, carborane, metallopolyborane and metallocarborane compounds, as described in more detail below.

As known to those skilled in the art, the term "polyborane" refers compounds of boron and hydrogen (i.e., boron hydrides) having more than one boron atom.

The simplest borane is $BH_3$, which is unstable at atmospheric pressure and becomes diborane ($B_2H_6$) as gas at normal pressures. This is in turn converted to higher boranes, i.e., penta, deca, and the like, by condensation. Exemplary hydrolytically stable polyboranes in accordance with the invention include pentaborane(9) $B_5H_9$, pentaborane(11) $B_5H_{11}$, hexaborane(10) $B_6H_{10}$, hexaborane(12) $B_6H_{12}$, octaborane(12) $B_8H_{12}$, octaborane(10) $B_8H_{10}$, nonaborane(15) $B_9H_{15}$, decaborane(14) $B_{10}H_{14}$, decaborane(16) $B_{10}H_{16}$ and the like. Other polyboranes in accordance with the invention include borane anions represented by the general formula $[B_nH_n]^{-2}$, wherein n is an integer from 6 to 12, such as $B_{10}H_{10}^{-2}$ and $B_{12}H_{12}^{-2}$. These and other polyboranes are known in the art and are described in Earl L Muetterties, The Chemistry of Boron and Its Compounds (1967) and Boron Hydride Chemistry (E. Muetteries, ed. 1975). Accordingly, as used herein, the term polyborane refers to hydrolytically stable polyboranes, polyborane anions and derivatives thereof, described in more detail below. Preferably, the polyborane is a polyborane anion.

The term "carborane" refers to a subgroup of polyboranes wherein a BH unit has been formally replaced by an isoelectronic CH group. Thus, carboranes comprise boron, carbon and hydrogen. Exemplary carboranes in accordance with the invention are the hydrolytically stable dicarbo-closo-dodecarboranes $C_2B_{10}H_{12}$, i.e., 1,2-$C_2B_{10}H_{12}$ (o-carborane), 1,7-$C_2B_{10}H_{12}$ (m-carborane), and 1,12-$C_2B_{10}H_{12}$ (p-carboranes); dicarbo-nido-carboranes $C_2B_9H_{13}$, i.e., 1,2 and 1,7-$C_2B_9H_{13}$; and anions thereof, i.e., nido-1,2$C_2B_9H_{12}^{-2}$, nido-1,7-$C_2B_9H_{12}^{-2}$, nido-1,2-$C_2B_9H_{11}^{-2}$ and nido-1,7-$C_2B_9H_{11}^{-2}$. Other representative carboranes include small nido-carboranes such as $CB_5H_9$, $C_2B_4H_8$, $C_3B_3H_7$, $C_4B_2H_6$, and $C_2B_3H_7$; small closo-carboranes such as $C_2B_3H_5$, $C_2B_4H_6$, $C_3B_5H_7$, $CB_5H_7$; and intermediate closo-carboranes such as $C_2B_6H_8$, $C_2B_7H_9$, $C_2B_8H_{10}$, and $C_2B_9H_{11}$. These compounds are known in the art and are described in Carboranes (R. Grimes ed. 1970) and Gmelin Handbook of Inorganic and Organometallic Chemistry (8th ed. 1991). Similar to the term polyborane, the term carborane refers to carboranes, carborane anions, and derivatives thereof.

As known to those skilled in the art, polyboranes may be substituted at a boron atom, and carboranes at either a boron or carbon atom, by alkyl, alkylaryl, aryl, halogen, sulfide, di- and tri-alkylsubstituted amino groups, and the like. As used herein the term alkyl refers to $C_1$ to $C_{10}$ linear or branched carbon chains, aryl refers to cyclic aromatic groups, such as phenyl, naphthyl, and the like, and alkylaryl refers to alkyl substituted aryl groups.

The terms polyborane and carborane also refer to transition metal derivatives thereof, i.e., "metallocene" derivatives, which are also known to those skilled in the art. Metallocene derivatives are organometallic coordination compounds obtained as a cyclopentadienyl derivative of a transition metal or metal halide. Typically, the metal is bonded to the cyclopentadienyl ring ($C_5H_5^-$) by electrons moving in orbitals extending above and below the plane of the ring (pi bond).

Carboranes may also form metallocene coordination compounds. For example, the $B_9C_2H_{11}^{-2}$ ions have an open pentagonal face, closely resemble the cyclopentadienyl anion, and form complexes with transition metal ions just like the latter. That is, the $B_9C_2H_{11}^{-2}$ ions contain six electrons in five aromatic orbitals at the open pentagonal face. Accordingly, the $B_9C_2H_{11}^{-2}$ ions and their C-substituted derivatives produce a class of "sandwich" compounds in which a transition metal completes the icosahedron. Such compounds are known in the art and are also described in Carboranes (R. Grimes ed. 1970), Earl L Muetterties, The Chemistry of Boron and Its Compounds (1967) and Boron Hydride Chemistry (E. Muetteries, ed., 1975).

In one embodiment of the invention, boronated phosphoramidates are provided. As known to those skilled in the art, phosphoramidates are compounds having the general formula (—OP(O)(O—)NH—). The phosphoramidate is boronated with an aminoalkyl substituted polyborane, carborane, metallopolyborane or metallocarborane. The aminoalkyl substituent is represented by the formula —$(CHR^1)_xN(R)$—, wherein $R^1$ and R are each independently hydrogen, $C_1$ to $C_{10}$ linear or branched alkyl or alkylaryl, and x is an integer from 1 to 20.

Boronated phosphoramidates in accordance with the invention are represented by the formula (I)

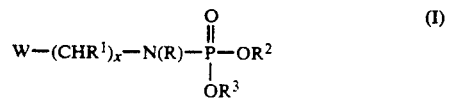

wherein:

R and $R^1$ are each independently selected from the group consisting of hydrogen, alkyl, and alkylaryl;

$R^2$ and $R^3$ are each independently selected from the group consisting of hydrogen, alkyl, alkylaryl, and aryl; and W is polyborane, carborane, metallopolyborane or metallocarborane, and wherein x is an integer from 1 to 20.

Illustrative of boronated phosphoramidates in accordance with this embodiment of the invention are:

(1) Dimethyl N-methyl-N-(o-carboranylmethyl) phosphoramidate;

(2) Diethyl N-methyl-N-(o-carboranylmethyl) phosphoramidate;

(3) Diethyl N-methyl-N(m-carboranylmethyl) phosphoramidate;

(4) Dimethyl N-methyl-N-(p-carboranylmethyl) phosphoramidate;

(5) Diisopropyl N-methyl-N-(p-{1-butyl} carboranylmethyl)-phosphoramidate;

(6) Diethyl N-methyl-N-(o-{1-methyl} carboranylethyl)-phosphoramidate;

(7) Di-n-propyl N-ethyl-N-(2-(dodecahydrododecaborato}ethyl)-phosphoramidate, disodium salt; and (8) Dimethyl N-methyl-N-(2-{decahydrodecaborato}ethyl)-phosphoramidate, diammonium salt.

In another embodiment of the invention, boronated nucleosides are provided. The term "nucleotide" is a term well-known in the art which is used to refer to the monomeric units of nucleic acids. Typically, nucleotides are described as compounds comprising a nitrogenous heterocyclic base, which is a derivative of either pyrimidine or purine; a pentose; and a molecule of phosphoric acid. The major nucleotides are deoxyribonucleotide (i.e., DNA) and ribonucleotide (i.e., RNA).

The compounds within each of the two major types of nucleotides DNA and RNA differ from each other in their nitrogenous bases. The base components of nucleotides are discussed in more detail below. The two types of nucleic acids also differ with regard to their pentose components. For example, deoxyribonucleotides contain as their pentose component 2'-deoxy-D-ribose, whereas ribonucleotides contain D-ribose. Both sugars occur as furanose forms in nucleotides.

The two classes of nitrogenous bases found in nucleotides are the heterocyclic compounds pyrimidine and purine. Three pyrimidine derivatives, uracil, thymine, and cytosine and two purine derivatives adenine and guanine constitute the major nitrogenous bases found in nucleotides. Adenine, guanine, cytosine and thymine are the bases characteristic of the deoxyribonucleotide units. Similarly, adenine, guanine, cytosine and uracil are the major base components of ribonucleotide units.

In nucleotides, the pentose is joined to the base by a β-N-glycosyl bond between carbon atom 1 of the pentose and nitrogen atom 9 of the purine bases or nitrogen atom 1 of pyrimidine bases. The phosphate group of nucleotides is in ester linkage with carbon 5 of the pentose. Nucleotides, also referred to as phosphate esters, include 5' mono-, di- and triphosphates.

When the phosphate group of a nucleotide is removed by hydrolysis, the remaining structure is known in the art as a nucleoside. Thus, typically the term "nucleoside" refers to a purine or pyrimidine base, and analogues thereof, linked to a pentose. Nucleosides, therefore, have the same structure as nucleotides with the phosphate group absent.

The boronated nucleosides of the present invention include the pentose and base structure described above, and a boronated phosphoramidate according to the formula (I) above, wherein $R^2$ or $R^3$ or both is substituted with a nucleoside structure. The boronated phosphoramidate substituent may be, for example, at the 2', 3', or 5' oxygen of the nucleoside pentose.

Illustrative of boronated nucleosides in accordance with this embodiment of the invention are:

(9) Thymidine-3'-O-[ethyl(N-methyl-N-{2-(o-carboranylethyl)})]-phosphoramidate;

(10) Guanosine-3'-O-[ethyl(N-methyl-N-{2-(o-carboranylethyl)})]-phosphoramidate;

(11) 2'-Deoxycytidine-3'-O-[ethyl(N-methyl-N-{(2-(o-carboranylethyl)})]-phosphoramidate;

(12) Thymidine-3'-O-[ethyl(N-methyl-N-{2-(1,2-dicarbonidoundecaboranyl)ethyl)})]-phosphoramidate anion; and

(13) Adenosine-3'-O-[ethyl(N-methyl-N-{2-(1,2-dicarbonidoundecaboranyl)ethyl)})]-phosphoramidate, tetramethylammonium salt.

Additionally, molecules and macromolecules comprising multimers of two or more nucleosides, which may be linked via a 3'-5' phosphate ester, e.g. oligonucleotides (the terms "oligonucleotides" and "polynucleotides" being used interchangeably herein), and comprising one or more boronated nucleosides are also the subject of the present invention. Accordingly, in yet another embodiment of the invention, a boronated oligonucleotide is provided comprising a chain of natural or modified ribonucleotides or deoxyribonucleotides, at least one nucleotide of which comprising a boronated nucleoside phosphoramidate as described above.

Illustrative of boronated oligonucleotides in accordance with this embodiment of the invention are:

(14) Dodecathymidylyl-(N-methyl-N-(o-(1-methyl)-carboranylethyl)-phosphoramidate;

(15) Undecaguanyl-(N-methyl-N-(o-(1-methyl)carboranylethyl)-phosphoramidate;

(16) Hexadecacytidylyl-(N-methyl-N-(o-(1-methyl)-carboranylethyl)-phosphoramidate;

(17) ApTpCpGpTpTpTpAp*T where p=normal phosphate and p*=N-ethyl-N-(1,7-dicarboclosododecaboranyl)methylphosphoramidate; (SEQ ID No. 1)

(18) Tp*Ap*Tp*Gp*Cp*Ap*Tp*Gp*Ap*Ap*Cp*Cp*Gp*Tp*T where p*=N-butyl-N-(6-[{1-propyl}1,12-dicarboclosododecaboranyl])hexyl-phosphoramidate; (SEQ ID No. 2)

(19) Tp'Tp'Ap'Ap'Ap'Tp*Tp*Tp*Ap*Ap* where p'=thiophosphate, p*=N-methyl-N-[2-(o-(1-methyl) carboranylethyl)] phosphoramidate; (SEQ ID No. 3)

(20) Cp*Cp*Cp*Gp*Gp*Gp*CpCpCpGpGpGp where p=normal phosphate and p*=N-ethyl-N-(1,7-dicarboclosododecaboranyl)methyl-phosphoramidate; (SEQ ID No. 4)

(21) Tp'Tp'Tp'Tp'Tp'Tp'Tp'Tp*Tp*Tp*Tp*Tp*T where p'=N-methyl-N-{2-(1,2-dicarbonidoundecaboranyl) ethyl)}]-phosphoramidate, ammonium salt and p*=N-butyl-N-(6-[{1-propyl} 1,12-dicarboclosododecaboranyl])hexyl-phosphoramidate; (SEQ ID No. 5) and

(22) Ap'Tp'Cp'Gp'Tp'Gp'Ap*Tp*Ap*Cp*Gp*T where p'=N-ethyl-N-(1,7-dicarboclosododecaboranyl)methyl-phosphoramidate and p*=N-ethyl-N-(2-(dodecahydrododecaborato)ethyl)-phosphoramidate, disodium salt (SEQ ID No. 6).

Oligonucleotides having phosphoramidate linkages in accordance with the invention can be synthesized in accordance with methods that are well known in the art. Such methods include the H-phosphonate method as described in B. C. Froehler et al., (1986) Tetrahedron Lett. 27, 469–472 and P. J. Garegg, et al., (9186) Tetrahedron Lett. 27, 4051–4054. The length of the oligonucleotide is not critical, as modern synthetic techniques and splicing techniques have made synthetic oligonucleotides of considerable length feasible. Thus, the oligonucleotide may for example be 2 to 3 nucleotides long, 2 to 18 nucleotides long, 2 to 30 nucleotides long, 2 to 50 nucleotides long, or 50 or more nucleotides long.

Oligonucleotides containing boronated phosphoramidates or nucleosides may alternatively be prepared, with boronation occurring randomly, in essentially the same manner as the phosphoramidate or nucleoside, but with an oligonucleotide substituted for the nucleoside. For example, in such a reaction, the 3' terminus of the oligonucleotides may be immobilized to a solid support (e.g., controlled pore glass), the 5' terminus protected as the dimethyltrityl ether, and amino groups on bases protected with isobutyryl groups.

Derivatives of the oligonucleotides and polynucleotides may additionally be formed by incorporating normal, i.e., phosphodiester, and modified phosphodiester backbones, in addition to the carbonyl phosphoramidate backbone as described above. Phosphodiester backbones can be synthesized in accordance with methods well known in the art, including the phosphite method and the phosphotriester method, 1 Chemistry of Nucleosides and Nucleotides, 294ff (L. Townsend ed. 1988). Modified backbones include modifying internucleotide phosphodiester linkages in the chain, for example, to the methylphosphonate, the phosphotriester, the phosphorothiaote, the phosphorodithioate, and other phosphoramidate all as is known in the art.

Additional synthetic analogues of the nucleosides, nucleotides, and oligonucleotides of the present invention may be formed by otherwise modifying the 3' or 5' end of the nucleoside, and any 2' hydroxyl groups. Groups that can be added to the 3' or 5' end vary widely, from relatively inert protecting groups to reactive groups or groups with special properties to obtain desirable physical, chemical, or biochemical effects.

A wide variety of protecting groups can be substituted on the 2', 3', and 5' hydroxy groups, such as the triphenylmethyl (trityl) group and its derivatives on the 5' hydroxy group, and acetyl, benzoyl, or the 3'-o-succinyl group on the 3' hydroxy group, as is know in the art. See 1 Chemistry of Nucleosides and Nucleotides, 287-92 (L. Townsend ed. 1988). In general, the 5' hydroxy group is protected with an acid labile group and the 3' hydroxy group is protected with an acyl group. Id. at 289 (When the 5' hydroxyl group is protected with an acid labile group such as mono- and dimethoxytrityl, the 3'-hydroxyl group of deoxynucleosides can be protected with acyl groups). In general, a 2' hydroxy group is protected as a methyl ether, protected with a silyl group, or the 2' and 3' hydroxy groups may be protected together as an acetal.

Nucleosides, nucleotides and oligonucleotides may also be protected at the base, for example, at the amino group of guanine, cytidine, and adenine, or the carbonyl group of guanine, hypoxanthine, uracil, or thymine. A wide variety of base protecting groups are known in the art and are readily available.

Reactive groups or groups with special properties may also be attached at the 3' or 5' position. For example, analogs may be formed by joining an intercalating agent to oligonucleotides and polynucleotides in the manner described in U.S. Pat. No. 4,835,263 to Nguyen et al. (the disclosure of this and all other patent references cited herein is incorporated by reference).

The invention also provides methods for preparing the boronated compounds wherein a phosphoramidate is reacted with an aminoalkyl substituted polyborane, carborane, metallopolyborane or metallocarborane as described above, i.e., of the formula W—$(CHR^1)_xN(-R)$—, wherein W is a polyborane, carborane, metallopolyborane or metallocarborane as described above; $R^1$ and R are each independently hydrogen or $C_1$ to $C_{10}$ linear or branched alkyl or alkylaryl; and x is an integer from 1 to 20.

The phosphoramidate may be prepared in any of the ways known in the art for synthesizing such compounds. For example, the phosphoramidate may be prepared by an H-phosphonate procedure such as that set forth by B. C. Froehler et al., (1986) Tetrahedron Lett. 27, 469-472 and P. J. Garegg, et al., (9186) Tetrahedron Lett. 27, 4051-4054. In this procedure, an H-phosphonate is reacted with carbon tetrachloride ($CCl_4$) in the presence of an amine, such as the tertiary amine triethylamine, to provide a phosphochloridate. The phosphochloridate is then reacted with the aminoalkyl substituted polyborane, carborane, metallopolyborane or metallocarborane to give a boronated compound.

The compounds of the present invention may have pharmaceutical activity and be useful in treating mammals (e.g., human, cat, dog, cow, horse, mouse) suffering from one or more of several maladies. It is believed, for example, that the preferential localization of boron compounds in the neoplasm of tumor cells will allow the use of boron-10 neutron capture therapy (BNTC) for the destruction of tumor cells. Moreover, the dual effect of this therapeutic regimen may lower the therapeutically effective amounts of the pharmaceutically active agents, and thereby reduce the deleterious side effects that often accompany the use of such agents. Thus, the present invention provides methods for treating tumor-bearing mammals in which the mammal is administered a boronated nucleoside as described herein and then exposed to thermal neutron radiation. The thermal neutron radiation is administered in an amount and in a manner effective for $^{10}B$ located in a tumor by virtue of the administration of the compound of the present invention to the subject to capture a neutron, decay, and release an alpha particle in cells of the tumor.

The boronated compounds of the present invention may be administered per se or in the form of a pharmaceutically acceptable salt. When used in medicine, the salts of the boronated compounds of the invention should be both pharmacologically and pharmaceutically acceptable, but non-pharmaceutically acceptable salts may conveniently be used to prepare the free active compound or pharmaceutically acceptable salts thereof and are not excluded from the scope of this invention. Such pharmacologically and pharmaceutically acceptable salts include, but are not limited to, those prepared from the following acids: hydrochloric, hydrobromic, sulphuric, nitric, phosphoric, maleic, acetic, salicylic, p-toluenesulfonic, tartaric, citric, methanesulphonic, formic, malonic, succinic, naphthalene-2-sulphonic and benzenesulphonic. Also, pharmaceutically acceptable salts can be prepared as alkaline metal or alkaline earth salts, such as sodium, potassium or calcium salts of the carboxylic acid group. Thus, the present invention also provides pharmaceutical formulations, both for veterinary and for human medical use, which comprise the boronated compounds with one or more pharmaceutically acceptable carriers thereof and optionally any other therapeutic ingredients. The carrier(s) must be pharmaceutically acceptable in the sense of being compatible with the other ingredients of the formulation and not unduly deleterious to the recipient thereof.

The formulations include those suitable for oral, rectal, topical, nasal, ophthalmic or parenteral (including subcutaneous, intramuscular and intravenous) administration. Formulations suitable for oral and parenteral administration are preferred.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier, a finely divided solid carrier, or both, and then, if necessary, shaping the product into desired formulations.

Formulations of the present invention suitable for oral administration may be presented as discrete units such as capsules, cachets, tablets or lozenges, each containing a predetermined amount of the potentiating agent as a powder or granules; or a suspension in an aqueous liquor or non-aqueous liquid such as a syrup, an elixir, an emulsion or a draught.

A tablet may be made by compression or molding, optionally with one or more accessory ingredients.

Compressed tablets may be prepared by compressing in a suitable machine, with the active compound being in a free-flowing form such as a powder or granules which is optionally mixed with a binder, disintegrant, lubricant, inert diluent, surface active agent or dispersing agent. Molded tablets comprised of a mixture of the powdered active compound with a suitable carrier may be made by molding in a suitable machine.

A syrup may be made by adding the active compound to a concentrated aqueous solution of a sugar, for example sucrose to which may also be added any accessory ingredient(s). Such accessory ingredient(s) may include flavorings, suitable preservatives, an agent to retard crystallization of the sugar, and an agent to increase the solubility of any other ingredient, such as a polyhydric alcohol, for example glycerol or sorbitol.

Formulations suitable for parenteral administration conveniently comprise a sterile aqueous preparation of the active compound, which is preferably isotonic with the blood of the recipient.

Nasal spray formulations comprise purified aqueous solutions of the active compound with preservative agents and isotonic agents. Such formulations are preferably adjusted to a pH and isotonic state compatible with the nasal mucous membranes.

Formulations for rectal administration may be presented as a suppository with a suitable carrier such as cocoa butter, or hydrogenated fats or hydrogenated fatty carboxylic acids.

Ophthalmic formulations are prepared by a similar method to the nasal spray, except that the pH and isotonic factors are preferably adjusted to match that of the eye.

Topical formulations comprise the active compound dissolved or suspended in one or more media such as mineral oil, petroleum, polyhydroxy alcohols or other bases used for topical pharmaceutical formulations. The addition of other accessory ingredients, vide infra, may be desirable.

In addition to the aforementioned ingredients, the formulations of this invention may further include one or more accessory ingredient(s) selected from diluents, buffers, flavoring agents, binders, disintegrants, surface active agents, thickeners, lubricants, preservatives (including antioxidants) and the like.

A therapeutically effective amount of a boronated compound is in the range of about 0.1-100 mg/kg/day. The preferred range is about 0.5-50 mg/kg/day. More preferred is an amount in the range of about 1-10 mg/kg/day. When administered conjointly with other pharmaceutically active agents even less of the boronated nucleoside may be therapeutically effective.

Oligonucleotides of the present invention which are capable of binding to polyribonucleic acid or polydeoxyribonucleic acid may be useful as antisense agents in the same manner as conventional antisense agents. See generally Antisense Molecular Biology and S-oligos, Synthesis 1 (Oct. 1988) (published by Synthecell Corp., Rockville, Md.); 2 Discoveries in Antisense Nucleic Acids (C. Brakel and R. Fraley eds. 1989) Antisense agents of the present invention may be used by contacting an antisense agent which is capable of selectively binding to a predetermined polydeoxyribonucleic acid sequence or polyribonucleic acid sequence to a cell containing such sequence (e.g., by adding the antisense agent to a culture medium containing the cell) so that the antisense agent is taken into the cell, binds to the predetermined sequence, and blocks transcription, translation, or replication thereof. The requirements for selective binding of the antisense agent are known (e.g., a length of 17 bases for selective binding within the human genome).

The invention is explained in greater detail in the following non-limiting Examples, in which $\mu l$=microliters, ml=milliliters, mmol=millimole, g=grams, mg=milligrams, and temperatures are given in degrees Centigrade unless indicated otherwise.

EXAMPLE 1

Diethyl N-methyl-N-(o-carboranylmethyl)phosphoramidate

N-Methylaminomethyl-o-carborane (0.37 g., 1.97 mmol) and triethylamine (550 $\mu l$, approximately 4 mmol) were taken in anhydrous carbon tetrachloride ($CCl_4$) under nitrogen. To this solution, diethylphosphite (250 $\mu l$, 1.94 mmol) was added and the mixture was allowed to stir at room temperature. After 25.5 hours, the reaction mixture was diluted with $CH_2Cl_2$, washed twice with water, dried over sodium sulfate (anhydrous), filtered and the solvent was removed in vacuo to give crude diethyl N-methyl-N-(o-carboranylmethyl)phosphoramidate as a pale yellow oil (Yield=545 mg, 86.78%). The product was purified by flash chromatography on silica gel using a stepwise gradient beginning at 100% $CH_2Cl_2$ and ending at 15% MeOH in $CH_2Cl_2$. The product was further chromatographed on silica gel using the following gradient conditions: $CH_2Cl_2$:hexane (1:1, 11), $CH_2Cl_2$:hexane (3:1, 11), $CH_2Cl_2$ (100%), 2.5% MeOH in $CH_2Cl_2$ (750 ml) and 5% MeOH in $CH_2Cl_2$ (750 ml). The yield was 0.22 g, 35.03%.

$^1H$ nmr analysis ($CDCl_3$):$\delta$(ppm)=4.186, s, CH; 4.035, m, $CH_2$ (OEt); 3.775, br. s, $CH_2N$; 2.705, d, $^3J_{P,H}$=9.1 Hz, $NCH_3$, 1.322, dt, $^4J_{PH}$=0.7 Hz, $CH_3$ (OEt); 1.05-3.20, br, m, BH. $^{11}B$ nmr ($CDCl_3$): $\delta$=1.1 ppm, −5.2 ppm and −11.2 ppm (1:1:8). $^{31}P\{^1H\}$ nmr ($CDCl_3$): $\delta$=9.43 ppm, s.

EXAMPLE 2

Diethyl N-methyl-N-(o-(1-methyl) carboranylethyl)phosphoramidate

Diethylphosphite (18.4 $\mu l$, 0.14 mmol) and $CCl_4$ (0.5 ml) were taken in an nmr tube. To this solution, triethylamine (80 $\mu l$, 4 equivalent) was added and the reaction was followed by $^{31}P$ nmr. After complete conversion to phosphochloridate, N-methylaminoethyl-o-(1-methyl)-carborane was added. $^{31}P$ nmr indicated complete conversion to diethyl N-methyl-N-(o-(1-methyl)carboranylethyl)phosphoramidate. $^{31}P\{^1H\}$ nmr: $\delta$=9.30 ppm, s.

EXAMPLE 3

Dodecathymidylyl-(N-methyl-N-(o-(1-methyl) carboranylethyl)-phosphoramidate

Dodecathymidylyl-H-phosphonate oligonucleotide was synthesized at 1.0 $\mu$molar scale by using a Biosearch-Milligen 8750 DNA synthesizer according to the H-phosphonate protocol. After removing the last DMT group, the synthesized H-phosphonate oligomer anchored to the controlled pore glass (CPG) was manually treated with a solution of N-methyl-2-(1-methyl-o-carboranyl)ethyl)amine (200 mg) in $CCl_4$ (1 ml) and $CH_3CN$ (1 ml) containing triethylamine (150 $\mu l$) at room temperature for 24 hours. The CPG supported oligomer was isolated by centrifugation and thoroughly washed with methanol to remove excess amine. The oligocarboranylphosphoramidate was cleaved from the CPG by a mixture of concentrated $NH_4OH$ and MeOH (2 ml, 1:1, v/v) at room temperature for 5 hours and isolated by evaporation of the ammonical solution. For characterization, the product was quantitatively converted to dodecathymidylyl phosphate oligomer ($dT_{12}$) by acid hydrolysis (88% formic acid, 95° C., 15 minutes, Kirby, A. J.; Wassen, S. G., The Organic Chemistry of Phosphorus, Elseviex Publishing Co., Inc., New York, 1967, 294-296) and compared with an authentic sample by TLC (thin layer chromatography) and HPLC (high performance liquid chromatography).

EXAMPLE 4

Diethyl N-methyl-N-((1,2-dicarbanidoundecaboranyl)-methyl)-phosphoramidate, $Me_4N$ salt Diethylphosphite (8.28 µl, 0.064 mmol), $CH_3CN$ (0.2 ml) and $CCl_4$ (0.2 ml) were taken in an nmr tube. To this solution, triethylamine (35.8 µl, 4 equivalent) was added and the reaction was followed by $^{31}P$ nmr. After complete conversion to phosphochloridate (~15 minutes), N-methylaminomethyl-1,2 dicarbanidoundecaborane), tetramethylammonium salt (16.10 mg, 0.064 mmol) was added. The formation of Diethyl N-methyl-N-(1,2-dicarbanidoundecaboranyl)-methylphosphoramidate, $Me_4N$ salt was complete within 10–15 minutes. $^{31}P\{^1H\}$ nmr:∂=9.55 ppm, s.

EXAMPLE 5

Diethyl N-methyl-N(1,2-dicarbanidoundecarboranyl) methyl phosphoramidate, Piperidinium Salt Diethyl N-Methyl-N-((1,2-dicarboclosododecaboranyl)methyl)phosphoramidate (55 mg, 0.169 mmoles) in benzene (2 mL) was treated with piperidine (1 g, 11.74 mmoles) and the mixture was stirred at room temperature for 1 hour. After the removal of benzene on a rotary evaporator, the excess piperidine was removed by heating the reaction mixture under vacuum (80° C. at 4 torr) to give Diethyl N-Methyl-N-(1,2-dicarbanidoundecaboranyl)methylphosphoramidate, piperidinium salt. The piperidinium salt was recrystallized from aqueous methanol to yield 23.4 mg (36% yield). NMR Spectra(∂): $^{11}B$(acetone-d6)−9.6, −14.86, −18.00, −20.81, −32.10, −36.01; $^{31}P\{H\}$ (acetone-d6) 8.55 ppm, s.

The foregoing examples are illustrative of the present invention, and not to be construed as limiting thereof. The Invention is defined by the following claims, with equivalents of the claims to be included therein.

---

We claim:

1. A boronated compound according to the formula

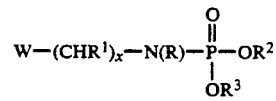

wherein:
  R and $R^1$ are each independently selected from the group consisting of hydrogen, alkyl, and alkylaryl;
  $R^2$ and $R^3$ are each independently selected from the group consisting of hydrogen, alkyl, alkylaryl, aryl, nucleosides and oligonucleotides; and
  W is polyborane or carborane, and wherein x is an integer from 1 to 20.

2. A boronated compound according to claim 1 wherein each of $R^2$ and $R^3$ is hydrogen, alkyl, alkylaryl, or aryl.

3. A boronated compound according to claim 1 wherein $R^2$ is hydrogen, alkyl, alkylaryl, or aryl and $R^3$ is a nucleoside.

4. A boronated compound according to claim 1 wherein each of $R^2$ and $R^3$ is an oligonucleotide.

5. A boronated compound according to claim 1 wherein W is a carborane.

6. A boronated compound according to claim 5 wherein said carborane is selected from the group consisting of $1,2\text{-}C_2B_{10}H_{12}$; $1,7\text{-}C_2B_{10}H_{12}$; $1,12\text{-}C_2B_{10}H_{12}$; $1,2\text{-}C_2B_9H_{13}$; $1,7\text{-}C_2B_9H_{13}$; $1,2\text{-}C_2B_9H_{12}^{-2}$; $1,7\text{-}C_2B_9H_{12}^{-2}$, $1,2\text{-}C_2B_9H_{11}^{-2}$; and $1,7\text{-}C_2B_9H_{11}^{-2}$.

7. A boronated compound according to claim 1 wherein $R^1$ is hydrogen and X is an integer from 1 to 5.

8. A boronated compound according to claim 1 wherein R is hydrogen, methyl or ethyl.

9. A boronated compound according to claim 1 wherein W is a metallopolyborane or a metallocarborane.

10. A boronated compound according to the formula

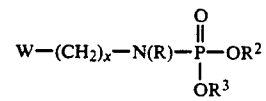

wherein:
  R is hydrogen or $C_1$ to $C_5$ linear alkyl;
  $R^2$ and $R^3$ are each independently selected from the group consisting of hydrogen, alkyl, alkylaryl, aryl, nucleosides and oligonucleotides; and
  W is a carborane, and wherein x is an integer from 1 to 5.

11. A boronated compound according to claim 10 wherein each of $R^2$ and $R^3$ is hydrogen, alkyl, alkylaryl, or aryl.

12. A boronated compound according to claim 10 wherein $R^2$ is hydrogen, alkyl, alkylaryl, or aryl and $R^3$ is a nucleoside.

13. A boronated compound according to claim 10 wherein each of $R^2$ and $R^3$ is an oligonucleotide.

14. A boronated compound according to claim 10 wherein W is a metallocarborane.

15. A boronated compound selected from the group consisting of:
(a) Dimethyl N-methyl-N-(o-carboranylmethyl) phosphoramidate;
(b) Diethyl N-methyl-N-(o-carboranylmethyl) phosphoramidate;
(c) Diethyl N-methyl-N(m-carboranylmethyl) phosphoramidate;
(d) Dimethyl N-methyl-N-(p-carboranylmethyl) phosphoramidate;
(e) Diisopropyl N-methyl-N-(p-{1-butyl} carboranylmethyl)-phosphoramidate;
(f) Diethyl N-methyl-N-(o-{1-methyl} carboranylethyl)-phosphoramidate;
(g) Di-n-propyl N-ethyl-N-(2-(dodecahydrododecaborato}ethyl)-phosphoramidate, disodium salt;
(h) Dimethyl N-methyl-N-(2-{decahydrodecaborato}ethyl)-phosphoramidate, diammonium salt;
(j) Thymidine-3'-O-[ethyl(N-methyl-N-{2-(o-carboranylethyl)})]-phosphoramidate;
(k) Guanosine-3'-O-[ethyl(N-methyl-N-{2-(o-carboranylethyl)})]-phosphoramidate;
(l) 2'-Deoxycytidine-3'-O-[ethyl(N-methyl-N-{(2-(o-carboranylethyl)})]-phosphoramidate;
(m) Thymidine-3'-O-[ethyl(N-methyl-N-{2-(1,2-dicarbonidoundecaboranyl)ethyl)})]-phosphoramidate anion;
(n) Adenosine-3'-O-[ethyl(N-methyl-N-{2-(1,2-dicarbonidoundecaboranyl)ethyl)})]-phosphoramidate, tetramethylammonium salt.
(o) Dodecathymidylyl-(N-methyl-N-(o-(1-methyl)-carboranylethyl)-phosphoramidate;
(p) Undecaguanyl-(N-methyl-N-(o-(1-methyl)carboranylethyl)-phosphoramidate;
(q) Hexadecacytidylyl-(N-methyl-N-(o-(1-methyl)-carboranylethyl)-phosphoramidate;
(r) ApTpCpGpTpTpTpAp*T where p=normal phosphate and p*=N-ethyl-N-(1,7-dicarboclosododecaboranyl)methylphosphoramidate (SEQ ID No. 1);
(s) Tp*Ap*Tp*Gp*Cp*Ap*Tp*Gp*Ap-*Ap*Cp*Cp*Gp*Tp*T where p*=N-butyl-N-(6-[{1-propyl}1,12-dicarboclosododecaboranyl])hexyl-phosphoramidate (SEQ ID No. 2);
(t) Tp'Tp'Ap'Ap'Ap'Tp*Tp*Tp*Ap*Ap* where p'=thiophosphate, p*=N-methyl-N-[2-(o-(1-methyl) carboranylethyl)] phosphoramidate (SEQ ID No. 3);
(u) Cp*Cp*Cp*Gp*Gp*Gp*CpCpCpGpGpGp where p=normal phosphate and p*=N-ethyl-N-(1,7-dicarboclosododecaboranyl)methyl-phosphoramidate (SEQ ID No. 4);
(v) Tp'Tp'Tp'Tp'Tp'Tp'Tp'Tp*Tp*Tp*Tp*T where p'=N-methyl-N-{2-(1,2-dicarbonidoundecaboranyl) ethyl)})]-phosphoramidate, ammonium salt and p*=N-butyl-N-(6-[{1-propyl} 1,12-dicarboclosododecaboranyl])hexyl-phosphoramidate (SEQ ID No. 5); and (w) Ap'Tp'Cp'Gp'Tp'Gp'Ap*Tp*Ap*Cp*Gp*T where p'=N-ethyl-N-(1,7-dicarboclosododecaboranyl)methyl-phosphoramidate and p*=N-ethyl-N-(2-{dodecahydrododecaborato}ethyl)-phosphoramidate, disodium salt (SEQ ID No. 6).

16. A boronated compound according to claim 15 selected from the group consisting of:
(a) Dimethyl N-methyl-N-(o-carboranylmethyl) phosphoramidate;
(b) Diethyl N-methyl-N-(o-carboranylmethyl) phosphoramidate;
(c) Diethyl N-methyl-N(m-carboranylmethyl) phosphoramidate;
(d) Dimethyl N-methyl-N-(p-carboranylmethyl) phosphoramidate;
(e) Diisopropyl N-methyl-N-(p-{1-butyl} carboranylmethyl)-phosphoramidate;
(f) Diethyl N-methyl-N-(o-{1-methyl} carboranylethyl)-phosphoramidate;
(g) Di-n-propyl N-ethyl-N-(2-{dodecahydrododecaborato}ethyl)-phosphoramidate, disodium salt; and
(h) Dimethyl N-methyl-N-(2-{decahydrodecaborato}ethyl)-phosphoramidate, diammonium salt;

17. A boronated compound according to claim 15 selected from the group consisting of:
(j) Thymidine-3'-O-[ethyl(N-methyl-N-{2-(o-carboranylethyl)})]-phosphoramidate;
(k) Guanosine-3'-O-[ethyl(N-methyl-N-{2-(o-carboranylethyl)})]-phosphoramidate;
(l) 2'-Deoxycytidine-3'-O-[ethyl(N-methyl-N-{2-(o-carboranylethyl)})]-phosphoramidate;
(m) Thymidine-3'-O-[ethyl(N-methyl-N-{2-(1,2-dicarbonidoundecaboranyl)ethyl)})]-phosphoramidate anion;
(n) Adenosine-3'-O-[ethyl(N-methyl-N-{2-(1,2-dicarbonidoundecaboranyl)ethyl)})]-phosphoramidate, tetramethylammonium salt;
(o) Dodecathymidylyl-(N-methyl-N-(o-(1-methyl)-carboranylethyl)-phosphoramidate;
(p) Undecaguanyl-(N-methyl-N-(o-(1-methyl)carboranylethyl)-phosphoramidate; and
(q) Hexadecacytidylyl-(N-methyl-N-(o-(1-methyl)-carboranylethyl)-phosphoramidate.

18. A boronated compound according to claim 15 selected from the group consisting of:
(r) ApTpCpGpTpTpTpAp*T where p=normal phosphate and p*=N-ethyl-N-(1,7-dicarboclosododecaboranyl)methylphosphoramidate (SEQ ID No. 1);
(s) Tp*Ap*Tp*Gp*Cp*Ap*Tp*Gp*Ap-*Ap*Cp*Cp*Gp*Tp*T where p*=N-butyl-N-(6-[{1-propyl}1,12 -dicarboclosododecaboranyl])hexyl-phosphoramidate (SEQ ID No. 2);
(t) Tp'Tp'Ap'Ap'Ap'Tp*Tp*Tp*Ap*Ap* where p'=thiophosphate, p*=N-methyl-N-[2-(o-(1-methyl) carboranylethyl)] phosphoramidate (SEQ ID No. 3);
(u) Cp*Cp*Cp*Gp*Gp*Gp*CpCpCpGpGpGp where p=normal phosphate and p*=N-ethyl-N-(1,7-dicarboclosododecaboranyl)methyl-phosphoramidate (SEQ ID No. 4);
(v) Tp'Tp'Tp'Tp'Tp'Tp'Tp'Tp*Tp*Tp*Tp*T where p'=N-methyl-N-{2-(1,2-dicarbonidoundecaboranyl) ethyl)})]-phosphoramidate, ammonium salt and p*=N-butyl-N-(6-[{1-propyl} 1,12- dicarboclosododecaboranyl])hexyl-phosphoramidate (SEQ ID No. 5); and (w) Ap'Tp'Cp'Gp'Tp'Gp'Ap*Tp*Ap*Cp*Gp*T where p'=N-ethyl-N-(1,7-dicarboclosododecaboranyl)methyl-phosphoramidate and p*=N-ethyl-N-(2-(dodecahydrododecaborato}ethyl)-phosphoramidate, disodium salt (SEQ ID No. 6).

* * * * *

SEQUENCE LISTING (1) GENERAL INFORMATION:

(i) APPLICANT: Spielvogel, Bernard F.
                      Sood, Anup (ii) TITLE OF INVENTION:
       Boronated Phosphoramidate Compounds (iii) NUMBER OF SEQUENCES: 6

(iv) CORRESPONDENCE ADDRESS:
       (A) ADDRESSEE: Melissa B. Pendleton
       (B) STREET: P.O. Drawer 34009
       (C) CITY: Charlotte
       (D) STATE: North Carolina

---

-continued

SEQUENCE LISTING (E) COUNTRY: USA
       (F) ZIP: 28234

(v) COMPUTER READABLE FORM:
       (A) MEDIUM TYPE: Floppy disk
       (B) COMPUTER: IBM PC compatible
       (C) OPERATING SYSTEM: PC-DOS/MS-DOS
       (D) SOFTWARE: PatentIn Release #1.0, Version #1.25

(vi) CURRENT APPLICATION DATA:
       (A) APPLICATION NUMBER: US 07/911,218
       (B) FILING DATE: 10-JUL-1992
       (C) CLASSIFICATION:

(viii) ATTORNEY/AGENT INFORMATION:
       (A) NAME: Pendleton, Melissa B.
       (B) REGISTRATION NUMBER: 35,459
       (C) REFERENCE/DOCKET NUMBER: 5420-6

(ix) TELECOMMUNICATION INFORMATION:
       (A) TELEPHONE: 704-377-1561
       (B) TELEFAX: 704-334-2014

(2) INFORMATION FOR SEQ ID NO:1:

(i) SEQUENCE CHARACTERISTICS:
       (A) LENGTH: 9 base pairs
       (B) TYPE: nucleic acid
       (C) STRANDEDNESS: single
       (D) TOPOLOGY: linear (ii) MOLECULE TYPE: cDNA (ix) FEATURE:
       (A) NAME/KEY: misc_difference
       (B) LOCATION: replace(8, " ")
       (D) OTHER INFORMATION: /note= "the phosphate is N-ether-N-(1,7-dicarboclosododecarboranyl)methyl phosphoramidate"

(xi) SEQUENCE DESCRIPTION: SEQ ID NO:1:

ATCGTTTAT                                              9

(2) INFORMATION FOR SEQ ID NO:2:

(i) SEQUENCE CHARACTERISTICS:
       (A) LENGTH: 15 base pairs
       (B) TYPE: nucleic acid
       (C) STRANDEDNESS: single
       (D) TOPOLOGY: linear (ii) MOLECULE TYPE: cDNA (ix) FEATURE:
       (A) NAME/KEY: misc_difference
       (B) LOCATION: replace(1..14, " ")
       (D) OTHER INFORMATION: /note= "the phosphate is N-butyl-N-(6-[(1-propyl)1,12-dicarboclosododecaboranyl])hexyl phosphoramidate"

(xi) SEQUENCE DESCRIPTION: SEQ ID NO:2:

TATGCATGAA CCGTT                               15

(2) INFORMATION FOR SEQ ID NO:3:

(i) SEQUENCE CHARACTERISTICS:
       (A) LENGTH: 10 base pairs
       (B) TYPE: nucleic acid
       (C) STRANDEDNESS: single
       (D) TOPOLOGY: linear (ii) MOLEUCLE TYPE: cDNA (ix) FEATURE:
       (A) NAME/KEY: misc_difference
       (B) LOCATION: replace(1..5, " ")
       (D) OTHER INFORMATION: /note= "the phosphate is thiophosphate"

-continued
SEQUENCE LISTING (ix) FEATURE:
  (A) NAME/KEY: misc_difference
  (B) LOCATION: replace(6..10, " ")
  (D) OTHER INFORMATION: /note= "the phosphate is N-methyl-N-[2-o-(1-methyl)carboranylethyl)] phosphoramidate"

(xi) SEQUENCE DESCRIPTION: SEQ ID NO:3:

TTAAATTTAA    10

(2) INFORMATION FOR SEQ ID NO:4:

(i) SEQUENCE CHARACTERISTICS:
    (A) LENGTH: 12 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: misc_difference
    (B) LOCATION: replace(1..6, " ")
    (D) OTHER INFORMATION: /note= "the phosphate is N-ethyl-N-(1,7-dicarboclosododecarboranyl)methyl phosphoramidate"

(xi) SEQUENCE DESCRIPTION: SEQ ID NO:4:

CCCGGGCCCG GG    12

(2) INFORMATION FOR SEQ ID NO:5:

(i) SEQUENCE CHARACTERISTICS:
    (A) LENGTH: 13 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: misc_difference
    (B) LOCATION: replace(1..7, " ")
    (D) OTHER INFORMATION: /note= "the phosphate is N-methyl-N-{2-(1,2-dicarbonidoundecaboranyl)ethyl)})]phosphoramidate, ammonium salt"

(ix) FEATURE:
    (A) NAME/KEY: misc_difference
    (B) LOCATION: replace(8..12, " ")
    (D) OTHER INFORMATION: /note= "the phosphate is N-butyl-N-(6-[{1-propyl}1,12-dicarboclosododecaboranyl])hexyl phosphoramidate"

(xi) SEQUENCE DESCRIPTION: SEQ ID NO:5:

TTTTTTTTTT TTT    13

(2) INFORMATION FOR SEQ ID NO:6:

(i) SEQUENCE CHARACTERISTICS:
    (A) LENGTH: 12 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: misc_difference
    (B) LOCATION: replace(1..6, " ")
    (D) OTHER INFORMATION: /note= "the phosphate is N-ethyl-N-(1,7-dicarboclosododecaboranyl)methyl phosphoramidate"

(ix) FEATURE:
    (A) NAME/KEY: misc_difference
    (B) LOCATION: replace(7..11, " ")
    (D) OTHER INFORMATION: /note= "the phosphate

-continued
SEQUENCE LISTING is N-ethyl-N-(2-{dodecahydrododecaborato}ethyl)-phosphoramidate, disodium salt"

(xi) SEQUENCE DESCRIPTION: SEQ ID NO:6:

ATCGTGATAC GT    12